United States Patent
Logroscino et al.

Patent Number: 5,507,745
Date of Patent: Apr. 16, 1996

[54] OCCIPITO-CERVICAL OSTEOSYNTHESIS INSTRUMENTATION

[75] Inventors: Carlo Logroscino, Rome, Italy; Philippe Bancel, Paris, France; Michel Goube, Hardelot, France; Pierre Jerome, Paris, France; Jean-Luc Marienne, Berck sur Mer, France

[73] Assignee: Sofamor, S.N.C., Rang Du Fliers, France

[21] Appl. No.: 198,986

[22] Filed: Feb. 18, 1994

[51] Int. Cl.$^6$ .......................... A61B 17/70; A61B 17/68; A61B 17/80

[52] U.S. Cl. ................... 606/61; 606/60; 606/69

[58] Field of Search .................. 606/61, 60, 69, 606/70, 71

[56] References Cited

U.S. PATENT DOCUMENTS

| | | | |
|---|---|---|---|
| 4,815,453 | 3/1989 | Cotrel | 606/61 |
| 4,887,595 | 12/1989 | Heinig et al. | 606/61 |
| 5,127,912 | 7/1992 | Ray et al. | 606/61 |
| 5,360,429 | 11/1994 | Jeanson et al. | 606/61 |

FOREIGN PATENT DOCUMENTS

| | | | |
|---|---|---|---|
| 1410965 | 7/1988 | Russian Federation | 606/61 |
| 9307823 | 4/1993 | WIPO | 606/61 |

*Primary Examiner*—Stephen C. Pellegrino
*Assistant Examiner*—Scott B. Markow
*Attorney, Agent, or Firm*—Woodard, Emhardt, Naughton, Moriarty & McNett

[57] ABSTRACT

The instrumentation comprises two separate similar parts, namely a right part (1) and a left part (2), each formed by a cervical rod (3) having asperities and an elongate occipital plate (5) forming one piece with the rod and extending it toward the occiput (6) in the position of use, and adjustable means for anchoring the rod to the vertebrae and the plate to the occiput. Each part is so preangulated and shaped as to be adapted to the anatomy of the occipito-cervical connection. Each rod (3) has two rectilinear sections making therebetween an angle of between about 70° and 90°, one of the sections being connected to the occipital plate (5), which is bent so as to correspond to the curvature of the occipital shell. The invention permits conveniently adapting the distance between the rods (3) to the anatomy of the patient and reduces the overall size of the instrumentation, which enables projections under the skin of the occiput to be considerably reduced.

8 Claims, 5 Drawing Sheets

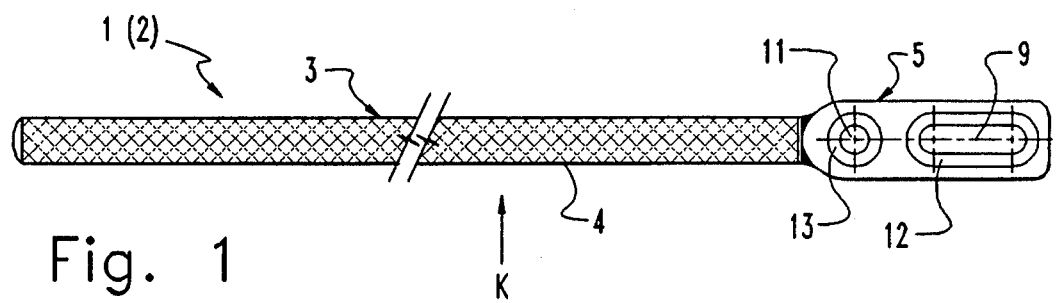
Fig. 1
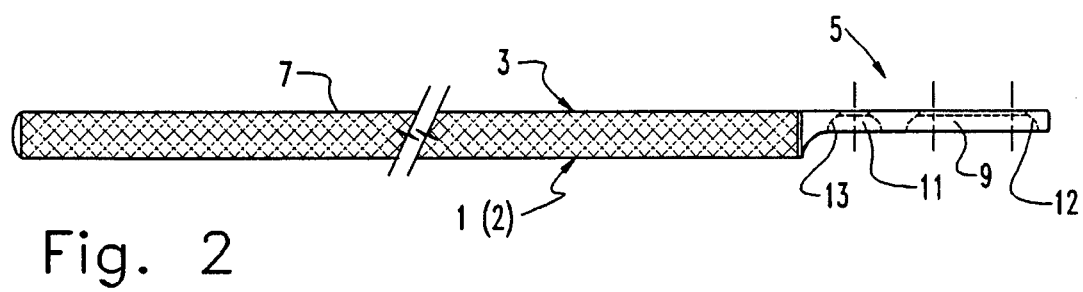
Fig. 2
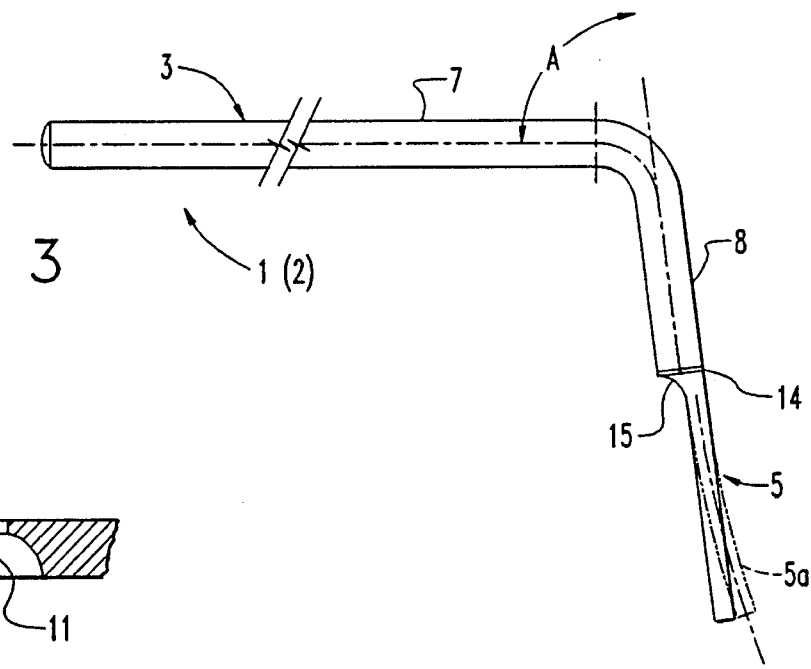
Fig. 3
Fig. 4

OCCIPITO-CERVICAL OSTEOSYNTHESIS INSTRUMENTATION

The present invention relates to an occipito-cervical osteosynthesis instrumentation and a hook adapted to be part of this instrumentation.

It is known that in the orthopaedic surgery of the cervical spine, when an instrumentation is required to realize an occipito-cervical artrodesis, the surgeon usually employs an instrumentation composed of plates and screws. There has thus been put on the market an assembly having the general shape of a horseshoe consisting of two rods in one piece with a curved connection plate, the rods being knurled and disposed in the cervical part, while the curved plate is in the occipital part. The fastening to the cervical vertebrae is achieved by thoracic and pediatric laminar hooks, whereas the connection of the plate to the occiput is achieved by a plurality of screws.

This device has a drawback in that it cannot be shaped in a satisfactory manner to the anatomical configuration of the patient, above all in the cervical part. Indeed, it is difficult to adapt the distance between the two rods in the cervical part while achieving an appropriate bending of the incurvate connection plate.

Further, in the orthopaedic surgery of the cervical segment, pathologies are encountered concerning the upper cervical vertebrae Atlas (CI) and Axis (C2). Among these pathologies there are essentially the degenerative pathology (cerviarthrosis) and the tumoral traumatic pathology. When an instrumentation is employed by the posterior approach, it is composed of either rods or plates, their common purpose being to isolate the pathological segment by connecting the occiput to the sound subjacent vertebrae. Thus various instrumentation rods, frames and plates are known, for example the Cotrel Dubousset rod, the Privat plate, the Roy Camille plate, etc. The means for connecting these various plates to the bone (occiput or vertebrae) comprise the following elements:

a) articular screws (inserted in the articular massives) and occipital screws, b) occipital screws and laminar hooks bearing against the vertebrae, c) metal wires constituting a bone lacing.

The screwed plates provide a solid occipito-cervical connection, but have some drawbacks: indeed, some are difficult to bend to the required curvature and have a fixed distance between the two rods of the cervical part. Others have a connection with the bone such as lacing, which is incompatible with laminectomies and lacks solidity, and are difficult to place in position.

Further, certain hooks employed in the prior instrumentations create, owing to the height of their head, a projection under the skin of the occiput of the patient which of course is better to eliminate.

It is also known from the French patent application 92 01 913 (2 687 561) to provide an occipito-cervical device in which the two cervical rods are extended by incurvate plates connected at their ends by a transverse connection plate. The assembly is fixed to the occiput by means of screws extending through openings in the connection plate, which permits a certain adjustment to the desired conformation.

However, here again, the possibilities of an anatomical adaptation are in fact limited, although this device affords the possibility of adjustment relative to the preceding device.

An object of the invention is to provide an occipito-cervical instrumentation which is arranged in such manner as to enable it to be better adaptable to the occipito-cervical anatomy of the patient, and which largely reduces projections under the skin.

According to the invention, the occipito-cervical instrumentation comprises:

a) two separate similar parts, namely a right and a left part, each formed by a cervical rod having asperities and an elongate occipital plate which forms one piece with said rod and extends said rod toward the occiput in the position of use, b) adjustable means for anchoring the rod to the vertebrae and the plate to the occiput, c) each part being so preangulated and shaped as to be adapted to the anatomy of the occipito-cervical connection.

Thus, in this assembly, the ends of the two occipital plates are not interconnected, which permits easily shaping them to the occipital anatomy of the patient, in the same way as the rods having asperities with which they respectively form one piece. The invention therefore affords the surgeon an improved flexibility and greater facility of adaptation of the assembly to the anatomical particularities of the patient.

This instrumentation may be advantageously completed by a transverse connection device which is positioned, either at the cervical level, or at the base of the occiput, by interconnecting the rods having asperities.

According to one embodiment of the invention, each rod has two substantially rectilinear sections making therebetween an angle of between about 70° and 90°, with a small angulation radius, one of the sections being shorter than the other and connected to the occipital plate, which is so bent as to correspond to the curvature of the occipital shell, the shortest rod section extending along the base of the occiput in the position of use.

A "small" radius is intended to mean for example a radius of about 4 mm.

This feature of an angulation with a small radius provides the possibility of achieving very short assemblies (C0-C1-C2, C0 being the occiput). Such assemblies therefore preserve the subjacent vertebra C3 and the following, which limits the surgical wound, avoids damaging the subjacent ligamentary complexes, and allows the patient maximum mobility which he would no longer have if the assembly had involved the vertebra C3 and the following vertebrae.

According to one feature of the invention, an oblong opening and a circular opening are formed in each elongate occipital plate and adapted to receive hooks and/or screws for fixing the plate to the occiput, it being possible to fix the hooks in different positions in the oblong openings.

In an alternative embodiment, the circular opening and the oblong opening may be replaced by three circular openings.

According to another feature of the invention, said adjustable anchoring means comprise, for each occipital plate, a hook having a laminar portion adapted to the shape of the occipito-cervical lamina, and a body which has a small height relative to its width and in which is provided a groove for receiving and guiding an occipital plate, a tapped hole being provided in said body in facing relation to the oblong opening or to the circular opening of the plate for receiving a screw fixing the plate to the hook.

The head of the screw has a shape corresponding to a spotfacing formed around the periphery of the oblong opening and can in this way be made flush with the end surface of the hook and with the surface of the plate.

The small thickness of the body of the hook achieved by means of this configuration reduces the overall size of the device and consequently in large part eliminates the project ion under the skin created by certain screws in prior instrumentations (screws having a U-shaped open body and an internally threaded plug or a screw having a closed body).

Further features and advantages of the invention will be apparent from the following description, with reference to the accompanying drawings which illustrate several embodiments of the invention by way of non-limitative examples.

In the drawings:

FIG. 1 is a longitudinal elevational view of a cervical rod having asperities extended by an occipital plate before the bending of the rod and representing a first embodiment of the invention.

FIG. 2 is a longitudinal elevational view of the rod-plate shown in FIG. 1 in another direction.

FIG. 3 is a side elevational view of the rod-plate shown in FIGS. 1 and 2, after its occipital part has been bent.

FIG. 4 is a half-sectional and half-elevational detail view of an opening in the occipital plate shown in FIGS. 1 to 3.

Figure 5:
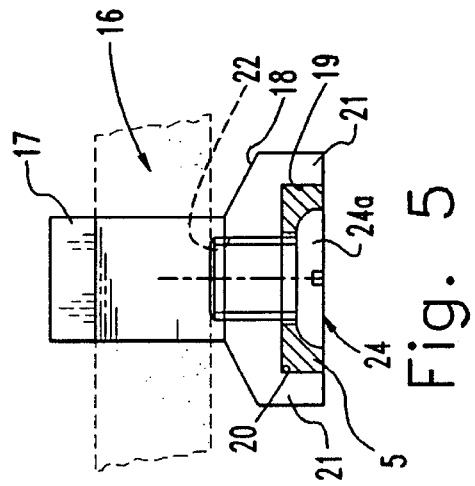
FIG. 5 is a half-sectional and half-elevational view to a larger scale of an embodiment of an occipital hook with which the plate shown in FIGS. 1 to 4 may be equipped for connecting it to the occiput.

The occipito-cervical osteosynthesis instrumentation shown in FIGS. 1 to 9 comprises two separate parts, namely a left part 1 and a right part 2 respectively (FIGS. 8 and 9 being views of the back of the patient), which are identical as manufactured. Each part is formed by a cervical rod 3 having asperities 4, such as knurling or diamond points, and an elongate occipital plate 5. The latter forms one piece with the rod 1 (2) and extends it toward the occiput 6 in the position of use.

The instrumentation further comprises adjustable means for anchoring the rod 1, 2 to the vertebrae C1, C2, C3 and the plate 5 to the occiput 6, each part 1 and 2 being so angulated and shaped as to be adapted to the anatomy of the occipito-cervical connection. Thus, in the illustrated embodiment, each rod 1, 2 consists of two substantially rectilinear sections 7 and 8 making therebetween an angle A of between about 70° and 90° (FIG. 3). The occipital section 8 of the rod has a length much shorter than that of the cervical section 7 of the rod and is connected to the occipital plate 5. The latter is so bent as to have the shape 5a (FIG. 3) to enable it to correspond to the curvature of the occipital shell. The rod section 8 connected to the plate 5 is adapted to extend along the base of the occiput 6 in the position of use.

Formed in each elongate plate 5 are an oblong opening 9 and a circular opening 11, the latter being provided in the vicinity of the junction between the plate 5 and the end portion 8 of the rod 3. Chamfers 12, 13 are machined around the openings 9 and 11 respectively.

The occipital plate 5 is connected to the adjacent section 8 of the rod 3 in a continuous manner by a junction portion 14 adjacent to the occipital bone 6 and by rounded fillets 15 on the opposite side. Thus, any change in level between the rod 3 and the plate 5 adjacent to the occiput is avoided.

Figure 7:
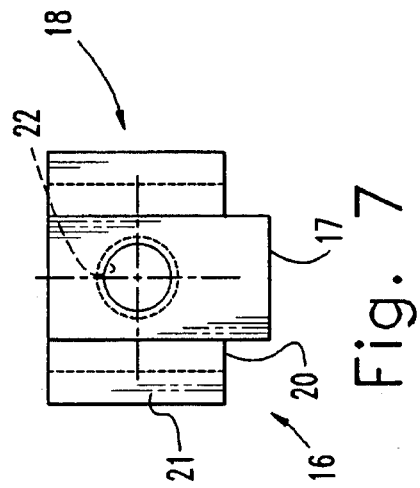
FIG. 7 is a top plan view of the occipital hook shown in FIGS. 5 and 6.
Figure 6:
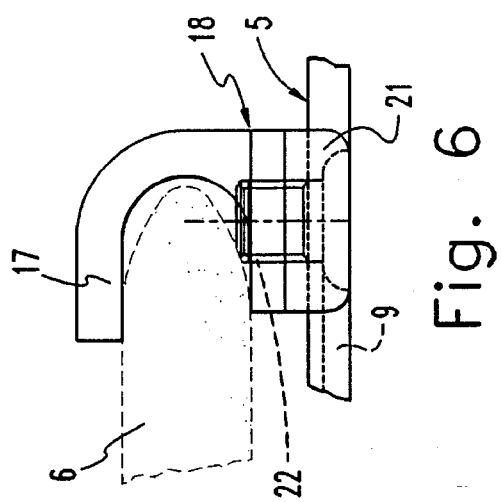
FIG. 6 is a side elevational view of the occipital hook shown in FIG. 5.

FIGS. 5 to 7 show a laminar hook 16 which comprises a laminar or plate portion 17 whose curvature is adapted to the thickness of the occipito-cervical shell, and a body 18 whose height h is small relative to its width L (FIG. 5). Arranged in the body 18 is a groove 19 receiving and guiding an occipital plate 5. The groove 19 is delimited by two parallel branches 21 of the body 18 defining with its bottom 20 a U-shaped channel which is shallow relative to its width. A tapped hole 22 is provided in the body 18 and opens out onto the bottom 20, and is in facing relation to the oblong opening 9 when the plate 5 is inserted between the branches 19 of the U. The plate 5 is fixed to the hook 16 by a screw 24 whose head 24a is so shaped and dimensioned that its periphery corresponds to the chamfer 12 around the oblong opening 9 and also corresponds to the chamfer 12 around the opening 11.

Consequently, the size of the head 24a may be reduced to such a thickness that its surface is flush with the surface of the plate 5 and with transverse end surfaces of the branches 21 of the body 18. A large reduction in the overall thickness of the system for assembling and anchoring in the bone results as compared to that possible with the afore-mentioned prior screws.

Thus, the screws 24 may be inserted both in the oblong openings 9 and in the circular openings 11 and in each case bear against the respective chamfer 12, 13 owing to the corresponding shape of their heads.

Figure 8:
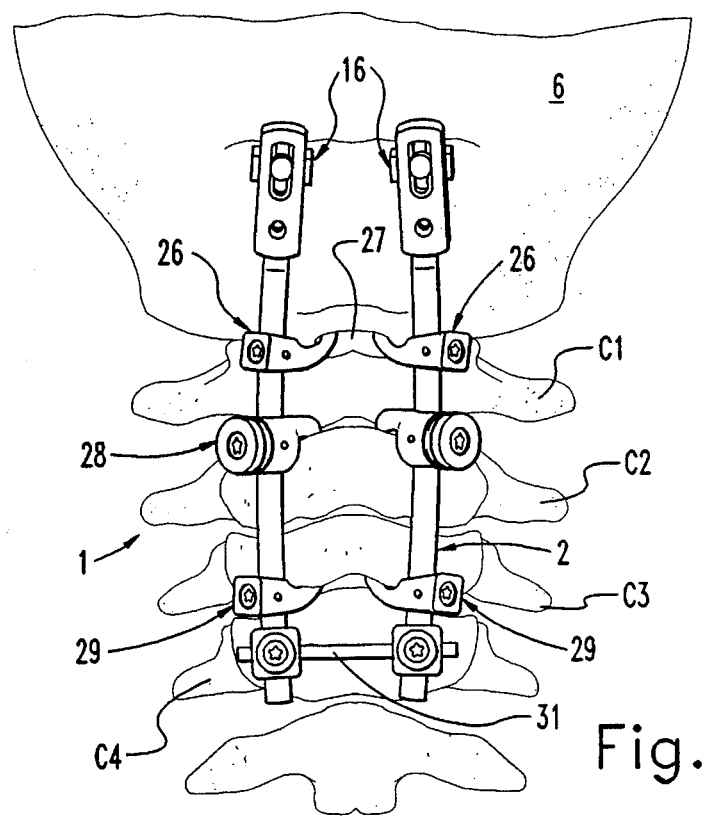
FIG. 8 is an elevational view to a smaller scale of an embodiment of the occipito-cervical instrumentation according to the invention, mounted on the first cervical vertebrae and on the occiput of a patient.
Figure 9:
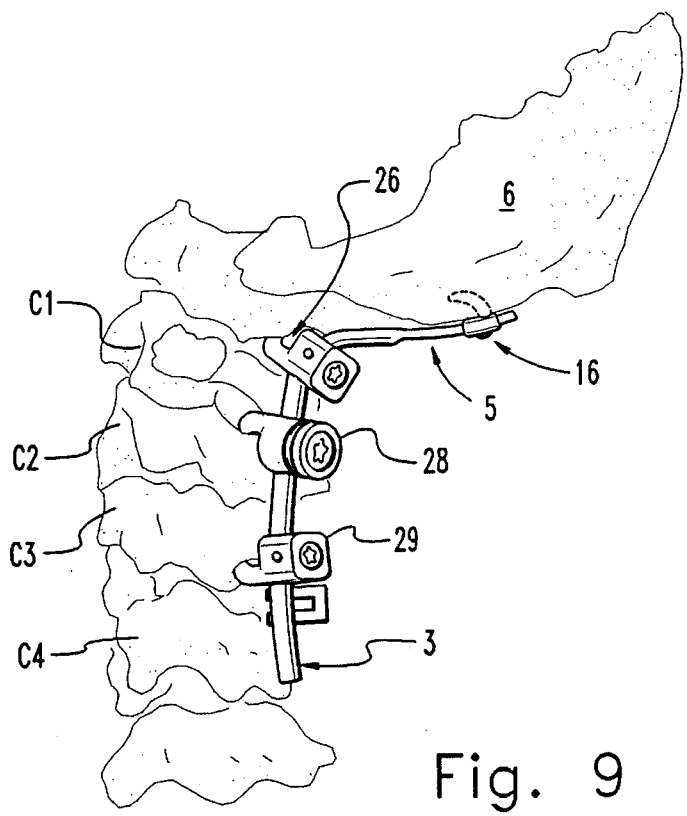
FIG. 9 is a side elevational view of the instrumentation, of the cervical vertebrae and of the occiput shown in FIG. 8.

An embodiment of a complete instrumentation, mounted on a cervical segment C1–C3 and on the occiput 6 is shown in FIGS. 8 and 9.

Hooks 16, whose laminar or plate portions 17 are inserted in openings formed in the occiput 6, are fixed to the respective plates 5 by screws 24. Other hooks 26 having a closed body are mounted on the rod sections 7 just before the bend that the rod sections 7 form with the terminal sections 8, the laminar portions of the hooks 26 extending into the foramen opening 27 at the base of the occiput 6 against which they bear. Screws fix the hooks 26 to the rods 3 in the known manner.

In the region of the cervical vertebrae C2, C3, the latter are fixed to the rods 3 by means of hooks 28 having an open body and a threaded internal plug (vertebra C2) and laminar hooks 29 having a closed body (vertebra C3), a transverse connection device 31 between the two rods 3 completing the instrumentation in the region of the vertebra C4. Such a transverse connection device is of known type and needs no detailed description.

Mounting the occipital hook 16 requires no specific instrumentation. The surgeon forms an opening in the occipital bone 6 (trepanation) so as to be able to insert the laminar portion 17 of the hook. This operation is carried out on both sides of the median line of the occiput 6 so as to permit mounting two plates 5. The bent plate 5a is then mounted in the groove 19 and fixed by a screw 24 to the hook 16. An accessory permits moving the occipital hook 16 toward the foramen hook 26 (the laminar portion of which is inserted in the foramen opening 27).

Figure 10:
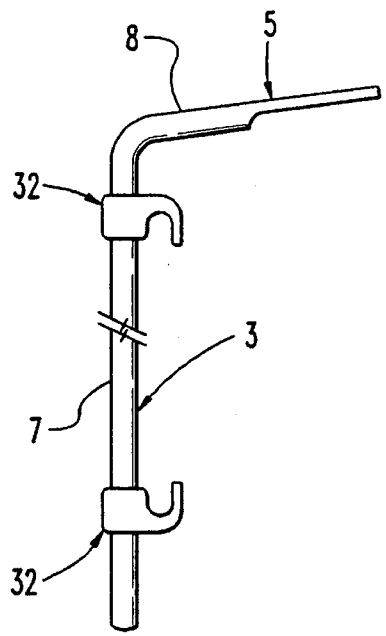
FIG. 10 is an elevational view to a smaller scale of the rod-plate shown in FIG. 3, the cervical rod being provided with two laminar hooks for fixing it to the cervical vertebrae.
Figure 11:
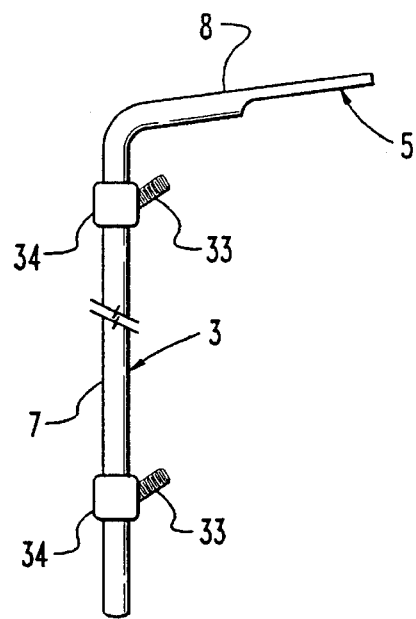
FIG. 11 is a view similar to FIG. 10 of the cervical rod provided with articular screws for fixing to the vertebrae.

FIGS. 10 to 15 shown various types of the fixing of each part 1, 2 of the instrumentation to the cervical vertebrae and to the occiput 6. In FIG. 10, the cervical part 7 of the rod 3 is provided with two cervical laminar hooks 32 of a known type which is open or closed. In Fig. 11, the same cervical part 7 of the rod 3 is provided with two articular screws 33 having a cortical thread adapted to the articular massive parts of the cervical vertebrae. The screws 33 penetrate these massive parts with a given inclination relative to the rod 3 and are connected by a connector 34 to the rod 3 in the known manner. The latter may be bent.

In the embodiments shown in FIGS. 10 and 11, the rods 3 may be long enough to reach the thoracic vertebra T2.

Figure 12:
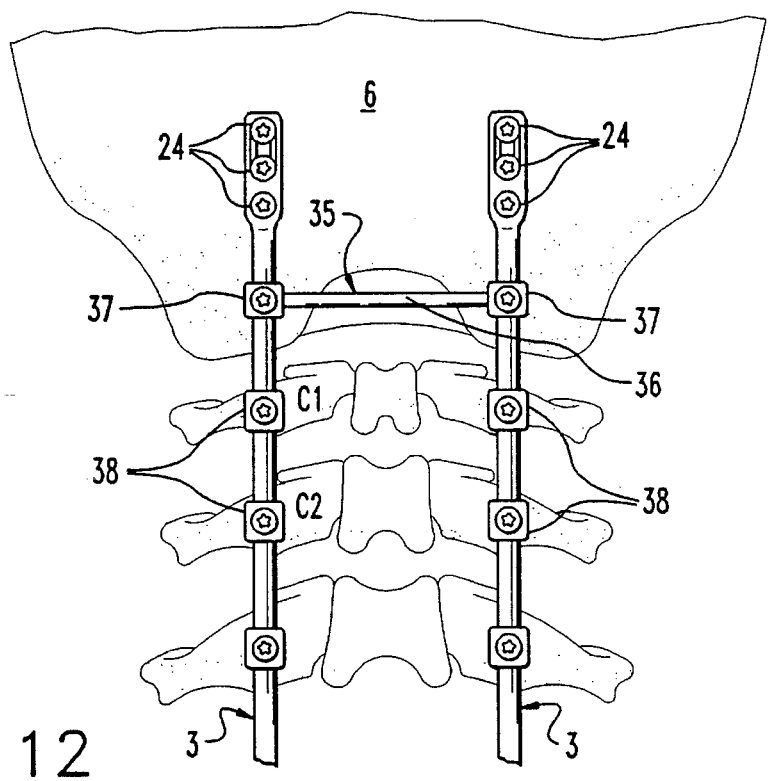
FIG. 12 is an elevational view of a second embodiment of the instrumentation according to the invention mounted on the first cervical vertebrae and on the occiput of a patient.

The instrumentation shown in FIG. 12 comprises for each part 1 and 2 three screws 24 for fixing the occipital plates 5 to the occiput 6, two of these screws 24 being inserted in each oblong opening 9. At the level of the foramen 27, the instrumentation comprises a transverse connection device 35 between the rods 3, this device being constituted by a transverse rod 36 and two cervical hooks 37 for securing the latter to the rod 36. Cervical hooks 38 complete the instrumentation in the region of the cervical vertebrae C1 and C2.

Figure 13:
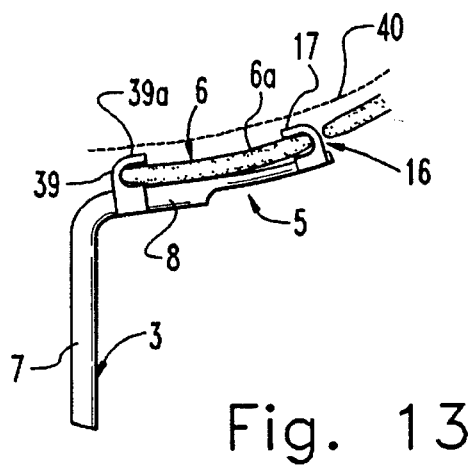
FIG. 13 is a partial side elevational view of a third embodiment of the instrumentation according to the invention in which the occipital part is fixed to the occiput by hooks.

In FIG. 13, the occipital plate 5 is secured to the occiput 6 by means of two laminar hooks, namely a first cervical hook 39, which is open or closed, has a large groove and is mounted on the section 8 having asperities of the rod 3, its laminar portion being disposed in the foramen opening 27, and an occipital hook 16.

The laminar or plate portion 17 of the hook 16 is engaged by the surgeon between the inner table 6a of the occiput 6 and the dura-mater 40. The hook 16 is fixed to the plate 5 by means of a screw 24.

Figure 14:
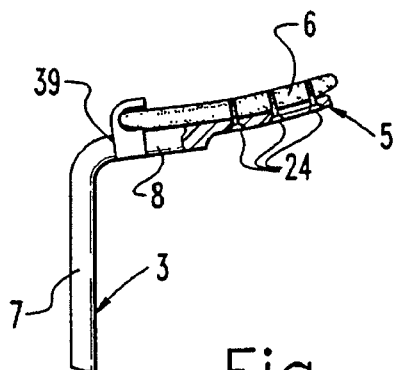
FIGS. 14 and 15 are partial side elevational views similar to FIG. 13 of two other embodiments of the instrumentation according to the invention.

FIG. 14 shows an alternative embodiment in which the occipital hook 16 is replaced by three screws 24 two of which are engaged in the oblong opening 9, the third being inserted in the circular opening 11 of the plate 5. As in the assembly shown in FIG. 13, a cervical hook 39 is engaged on the end part 8 of the rod 3 having asperities in the region of the foramen opening 27.

Figure 15:
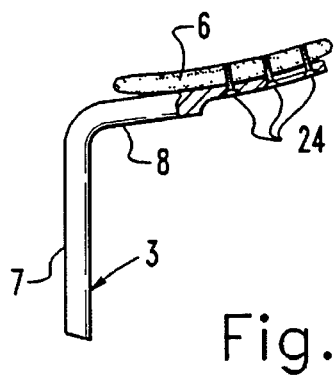

Lastly, the alternative embodiment shown in FIG. 15 differs from that shown in FIG. 14 in that the cervical hook 39 is eliminated, the plate 5 being fixed to the occiput 6 solely by the three screws 24.

Figure 16:
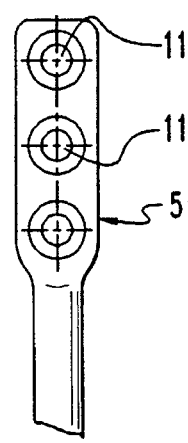
FIG. 16 is a partial elevational of an alternative embodiment of the rod-plate shown in FIG. 1.

The alternative embodiment shown in FIG. 16 comprises three circular openings 11 in the plate 5 which may be provided with screws 24 or hooks.

The rod 3 having asperities and the plate 5 are both bendable, provided this remains within the limits imposed by the elongation of the material and care is taken to avoid any initiation of a crack.

In addition to the advantages already mentioned, the instrumentation according to the invention has other advantages: thus, the fact that it has two rods and not a plate in one piece, on one hand permits an easier differentiated bending of each rod having asperities and, on the other hand, facilitates the adaptation to the considered specific mounting of the distance between the two rods 3. The transverse connection device 31 or 35 supports and reinforces the assembly, either in the cervical part or in the occipital part, or in both these regions.

Further, the two rods 3 may be employed indifferently in the left part and the right part of the occiput, since they are initially identical as manufactured, which affords the surgeon an additional facility.

Moreover, the presence of the rod section 8 in the occipital part and therefore its connection in the occipital part (and not in the cervical part), not only improves the performance as concerns fatigue of the part 1 or 2 of the instrumentation, but also enables the surgeon to employ either hooks or screws, or both, in the occipital part.

The advantages of the instrumentation according to the invention, explained hereinbefore, may be stated briefly as follows: bendability, variable distance between the two rods 3 having asperities, indifferent utilization of hooks and screws for the same type of mounting, reduced overall size which considerably reduces projections under the skin rof the occiput, possibility of placing a transverse connection device in the cervical and occipital part, covering of the instrumentation from the segment C0 to T2, and possibility of a very short assembly C0-C1-C2.

What is claimed is:

1. Occipito-cervical osteosynthesis instrumentation comprising:
    a) a part formed by a cervical rod and an elongate occipital plate forming one piece with said rod and extending it toward the occiput in the position of use, said occipital plate defining an opening therethrough,
    b) a hook having a laminar portion configured to engage the occipito-cervical lamina, and a body having a small height relative to the width of said body, a groove defined in said body for receiving said occipital plate, and a tapped hole defined in said body in facing relation to said plate,
    c) a screw for fixing said plate to said hook configured to extend through said opening in said occipital plate and threaded to engage said tapped hole,
    d) said part being so preangulated and shaped as to be adapted to the anatomy of the occipito-cervical junction.

2. Instrumentation according to claim 1, wherein:
    said oblong openings and said circular openings of said occipital plate each include chamfers defined therearound; and
    said screws for fixing said plate to said hook each include heads configured complementary to said chamfers and being so dimensioned as to be flush with a surface of said plate surrounding said oblong openings and said circular openings.

3. Instrumentation according to claim 1, wherein said plate has a thickness and said groove has a depth, wherein said thickness is at least equal to said depth.

4. Instrumentation according to claim 1, further comprising an oblong opening and a circular opening formed in said elongate occipital plate, at least one of said oblong opening and said circular opening configured to receive said screw for fixing said plate to said hook therethrough.

5. Instrumentation according to claim 4, further comprising a bone screw having bone engaging threads configured for threading into the occiput, and a head configured to be received within at least one of said oblong opening and said circular opening.

6. Instrumentation according to claim 5, further comprising a second bone screw having bone engaging threads configured for threading into the occiput, and a head configured to be received within said oblong opening when said head of said bone screw is also received within said oblong opening.

7. Occipito-cervical osteosynthesis instrumentation comprising:
    a part formed by a cervical rod and an elongate occipital plate forming one piece with said rod and extending toward the occiput in the position of use;

adjustable anchoring means for anchoring said rod to the vertebrae and said plate to the occiput in the position of use;

said rod having two substantially rectilinear sections, one of said sections being shorter than the other and connected to said occipital plate, said shorter rod section extending along the base of the occiput in the position of use, said sections forming an angle therebetween adapted to the anatomy of the occipito-cervical junction;

wherein said adjustable anchoring means includes hooks having a laminar portion adapted to be inserted at the base of the occipital bone in a foramen opening, said hooks being mounted on said shorter section of said rod which is connected to said occipital plate.

8. A method for mounting an occipito-cervical instrumentation to the occipito-cervical junction, comprising the steps of:

a) providing occipito-cervical instrumentation having a part formed by a cervical rod and an elongated occipital plate which forms one piece with the rod, an oblong opening and a circular opening defined in the plate, the part being so preangulated and shaped as to be adapted to the anatomy of the occipito-cervical junction;

b) forming an opening in the occipital bone;

c) providing a hook having a laminar portion adapted to be received within the opening in the occipital bone, and a head portion configured for receiving the occipital plate therein;

d) inserting the laminar portion of the hook in the opening formed in said occipital bone;

e) placing the occipital plate of the part in the head portion of the hook and fixing the plate thereto; and f) providing a bone engaging fastener and a connector;

g) fixing the cervical rod to at least one of the vertebrae by the bone engaging fastener connected to the rod by the connector.

* * * * *